(12) United States Patent
Graumann et al.

(10) Patent No.: US 9,055,912 B2
(45) Date of Patent: Jun. 16, 2015

(54) SUPPORTING DEVICE AND INTRA-OPERATIVE IMAGING DEVICE HAVING THE SUPPORTING DEVICE

(71) Applicant: SIEMENS AKTIENGESELLSCHAFT, Munich (DE)

(72) Inventors: Rainer Graumann, Hoechstadt (DE); Gerhard Kleinszig, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 163 days.

(21) Appl. No.: 13/932,169

(22) Filed: Jul. 1, 2013

(65) Prior Publication Data
US 2014/0003576 A1 Jan. 2, 2014

(30) Foreign Application Priority Data
Jun. 29, 2012 (DE) .......... 10 2012 211 330

(51) Int. Cl.
*A61B 6/00* (2006.01)
*A61B 6/03* (2006.01)

(52) U.S. Cl.
CPC ............. *A61B 6/4441* (2013.01); *A61B 6/4435* (2013.01); *A61B 6/035* (2013.01)

(58) Field of Classification Search
CPC ........ A61B 6/035; A61B 6/44; A61B 6/4429; A61B 6/4435; A61B 6/4425; A61B 6/4458
See application file for complete search history.

(56) References Cited

U.S. PATENT DOCUMENTS

| 6,203,196 | B1* | 3/2001 | Meyer et al. ............ 378/197 |
| 6,619,840 | B2* | 9/2003 | Rasche et al. ........... 378/197 |
| 6,940,941 | B2 | 9/2005 | Gregerson et al. |
| 6,969,194 | B1* | 11/2005 | Nafstadius ............ 378/197 |
| 7,490,982 | B2 | 2/2009 | Gregerson et al. |
| 8,303,181 | B2* | 11/2012 | Sukovic et al. ......... 378/197 |
| 8,348,506 | B2* | 1/2013 | Yorkston et al. ........ 378/196 |
| 8,662,750 | B2* | 3/2014 | Maschke ............... 378/198 |
| 2003/0072416 | A1* | 4/2003 | Rasche et al. ........... 378/197 |
| 2011/0280364 | A1* | 11/2011 | Maschke ............... 378/4 |

FOREIGN PATENT DOCUMENTS

| DE | 198 39 825 C1 | 10/1999 |
| DE | 10 2006 049 574 A1 | 4/2008 |
| DE | 10 2010 020 605 A1 | 11/2011 |

* cited by examiner

*Primary Examiner* — Thomas R Artman
(74) *Attorney, Agent, or Firm* — Laurence A. Greenberg; Werner H. Stemer; Ralph E. Locher

(57) ABSTRACT

A supporting device is provided for a radiation source and a radiation detector, as well as an imaging device having a supporting device. The supporting device contains a base unit, a guidance device with a first segment and a second segment, and a first support arm. The first segment is rotatably arranged at a first rotation connection at the first support arm. The first support arm is pivotably arranged at the base unit of the supporting device such that, by a pivot movement of the first support arm, the first segment can be moved from a first position in which the segments make contact with one another, into a second position in which the segments are separated from one another.

15 Claims, 2 Drawing Sheets

SUPPORTING DEVICE AND INTRA-OPERATIVE IMAGING DEVICE HAVING THE SUPPORTING DEVICE

CROSS-REFERENCE TO RELATED APPLICATION

This application claims the priority, under 35 U.S.C. §119, of German application DE 10 2012 211 330.4, filed Jun. 29, 2012; the prior application is herewith incorporated by reference in its entirety.

BACKGROUND OF THE INVENTION

Field of the Invention

The invention relates to an intra-operative imaging device, in particular for intra-operative use and a supporting device for the imaging device.

German patent DE 19839825 C1, corresponding to U.S. Pat. No. 6,203,196, discloses an X-ray diagnostic device which has an arc-shaped support for a radiation source and a radiation detector. The arc-shaped support is tiltable about a vertical and a horizontal axis. In this way, the irradiation direction for fluoroscopy can be selected within a large range.

The arc-shaped support has the form of a circular ring segment and can be extended to a circular support by bringing in a further circular ring segment. Therefore, the X-ray diagnostic device of German patent DE 19839825 C1 can also be used for creating computed tomography images, in that the radiation source and the radiation detector circle the object under investigation along the circular support during recording.

U.S. Pat. Nos. 6,940,941 B2 and 7,490,982 B2 disclose a mobile X-ray diagnostic device which has an O-shaped support. In order to be able to introduce an object under investigation into the interior of the O-shaped support, a segment of the O-shaped support is arranged to be detachable from another segment of the circular support or is pivotable or displaceable relative thereto. In this way, the X-ray diagnostic device can be moved toward the object under investigation and thereafter, the O-shaped support can be closed again. U.S. Pat. No. 7,490,982 B2 also discloses that the O-shaped support is tiltable about a horizontal axis as well as about a vertical axis to a limited extent.

For intra-operative uses of X-ray diagnostic devices, it is first required that the devices are usable in a flexible manner and, second, enable easy use and, in the confined, spatially limited environment of the surgical operating area, occupy as little space as possible.

BRIEF SUMMARY OF THE INVENTION

It is therefore an object of the present invention to provide a flexible X-ray diagnostic device which ensures good access to the patient and the operation environment.

The supporting device according to the invention has a base unit, a guidance device and a first support arm. A radiation source and a radiation detector can be displaceably arranged at the guidance device. The guidance device is configured so that the radiation source and the radiation detector are displaceable along a closed movement path at the guidance device. An object under investigation can be arranged within the closed movement path of the guidance device so that radiation emitted by the radiation source can pass though the object under investigation and fall on the radiation detector. The guidance device has at least one first and one second segment. The first segment is rotatably arranged at a first rotation connection at the first support arm and the first support arm is rotatable at the base unit of the supporting device such that, by a pivot movement of the first support arm, the first segment can be moved from a first position in which the movement path is closed into a second position in which there is an interruption in the movement path (curve). A gap between the segments creates the interruption of the movement path, so that the object under investigation can be introduced from a region outside the movement path, through the interruption in the movement path, into a region within the movement path. In other words, in the second position of the first support arm, an object under investigation can be introduced laterally through the gap between the segments into a region enclosed by the guidance device where the object under investigation can be transilluminated by the radiation source and a radiographic image can be recorded by the radiation detector.

The inventive imaging device thus contains the inventive supporting device and a radiation source, as well as a radiation detector.

Advantageously, therefore, during intra-operative use, an imaging device having a supporting device according to the invention can be moved laterally toward the operating table and over the patient. Thereafter, the first segment of the guidance device can be brought into the first position again, so that without changing the position of the patient, fluoroscopy or computed tomography can be carried out. In that the first segment is rotatably mounted at a first rotary connection at the first support arm, in the opened second position, the first segment can be turned away in order to enable easier access to the interior of the movement path, so that the object under investigation can be introduced more easily into the interior and, furthermore, access is simplified.

Thus, in a preferred embodiment, the supporting device according to the invention has a second support arm at which the second segment of the guidance device is arranged. The second segment is rotatably arranged at a second rotary connection at the second support arm. In the first position of the first segment in which the movement path of the guidance device is closed, the two rotary connections are arranged at the first and second support arm along a connecting axis, about which the guidance device can rotate. The connecting line between the two rotary connections has an intersection with a normal to the area enclosed by the movement path. In other words, in the simplest case, the connecting line or the first rotation axis extends through the area enclosed by the movement path or lies at a distance in front of or behind the area when the area is oriented substantially vertically.

It is herein advantageous that, with the movement path closed, the guidance device can be rotated about the connecting axis, so that the image recording device having the inventive supporting device is able to change the image plane of a recording by the rotation about the connecting axis. In that the connecting axis does not lie laterally in relation to the movement path, but rather extends through, in front of, or behind the area enclosed by the movement path, recordings of the portion of the object under investigation through which the connecting axis extends can be made at different first angles by rotating the guidance device. It is possible, at the same time, to rotate the guidance device through a larger angle if the rotation axis or connecting axis extends through the area enclosed by the movement path or at a small distance therebefore or therebehind, rather than being arranged laterally outside the movement path. For in the case of an object under investigation which has a substantially greater extent in one direction, for example, a patient on a couch and arranged within the movement path, compared with a rotation about a rotation axis arranged laterally, provided the half-axis of the movement path is of the same size, a rotation through a larger angle is possible before the guidance device comes into contact with the object under investigation or with the couch.

In an embodiment, the first support arm and the second support arm are detachably connected to the base unit.

By this means, it is advantageously possible to detach the guidance device, possibly together with the radiation source and the radiation detector, from the base unit and to mount the parts in another room at another base unit. The base unit can thus be constructed heavier and more stable, permitting the supply of more energy to the radiation source if the energy supply is provided in the base unit. The guidance device can also be configured to be correspondingly more stable, enabling for example, more precise positioning and, on recording of sectional images using an imaging device with the supporting device according to the invention, a higher peripheral speed of the radiation source and the radiation detector along the movement path.

In another embodiment, it is provided that the first and second support arms are rotatable about a common second rotation axis relative to the base unit of the supporting device. The second rotation axis is oriented at an angle to the first rotation axis such that the orientation of an area enclosed by the movement path is rotatable in space. In one possible embodiment, the first rotation axis is oriented perpendicularly to the second rotation axis.

It is therefore also possible, in an advantageous manner, to make recordings of the object under investigation at different angles in relation to the second rotation axis with an image recording device having the inventive supporting device.

In an embodiment, it can also be provided that the first and second support arms have devices which are configured for changing the distance between the base unit and the guidance device.

This makes it possible, in advantageous manner, to change the position of the guidance device in the surgical operating area in order to obtain freer access to the patient. At the same time, it is possible to change the position of the rotation axes in the space relative to the object under investigation, so that recordings of different portions of the object under investigation can be made from different directions without moving the object under investigation.

In a possible embodiment, the device for changing the distance is a telescopic extension.

A telescopic extension enables the guidance device to move along a first translation axis in a space-saving and repeatable manner.

In an embodiment, the supporting device has a device for movement at which the first and second support arm are arranged, wherein the device for movement is configured to move the support arms relative to the base unit in the direction of a second translation axis along one side of the base unit. The second translation axis is arranged at an angle, and not parallel, to the first translation axis. In an embodiment, through a movement along the second translation axis, the distance from the floor is altered and, in particular, the second translation axis can be oriented vertically.

The movement along the second translation axis advantageously enables the position of the guidance device to be changed in order to obtain easier access to the patient. Thus the height of the object under investigation can be changed. At the same time, it is possible to change the position of the rotation axes in space relative to the object under investigation so that recordings of different portions of the object under investigation can be made from different directions without moving the object under investigation. Furthermore, it is possible, in conjunction with a rotation of the guidance device about the second rotation axis, to scan an object under investigation in an upright position along the vertical axis.

In an embodiment, it is conceivable that the device for moving along a second translation axis is a linear rail.

A linear rail makes it possible, in a space-saving repeatable manner, to move the guidance device along a second translation direction.

In an embodiment, provided at the base unit of the supporting device are transport devices which are configured to move the guidance device along a third translation axis. The third translation axis is arranged at an angle, and not parallel, to the first and second translation axis. In particular, the third translation axis can be oriented horizontally and parallel to an operating table.

The movement along the third translation axis enables, in an advantageous manner, the position of the guidance device to be changed in the surgical operating area in order to obtain easier access to the patient. It is simultaneously possible to change the position of the rotation axes in space relative to the object under investigation, so that recordings of different portions of the object under investigation can be created from different directions without moving the object under investigation itself. By an arrangement of the third translation axis along the operating table in the direction of the greatest longitudinal extent of the object under investigation, a scan along the object under investigation is also possible by a movement along the third translation axis.

In an embodiment, the device has a motorized drive which is configured to move the supporting device along the first and/or second translation axis.

Motorized drives facilitate the movement of the supporting device with large masses and the provision of the large forces consequently required. Furthermore, movement by use of control elements which can be operated, for example, with a foot is possible, so that the sterility of the surgical operating area is not affected.

In an embodiment, the motorized drive has a control device which is configured to move the supporting device into a pre-definable position along the first and/or second and/or third translation axis.

With a control device of this type, which can be realized by a computer control system, it is advantageously possible to move the guidance device out of the surgical operating area and then later to return the guidance device back into precisely the same position so that, in the mean time, access can be gained to the patient without hindrance by the image recording device. It is also thereby possible to allow scans or other recording forms to run in a pre-programmed manner.

In an embodiment, the segments of the guidance device have an arc form.

An arc form advantageously unifies high stability with easy displaceability of the radiation source and of the radiation detector along the arc.

In a preferred embodiment, the closed movement path is circular in shape.

The circular movement path enables the radiation source and the radiation detector always to move at the same distance from one another, thereby significantly simplifying the evaluation of the data recorded by the radiation detector and enabling a constant radiation dose with a constant distance from the object under investigation if the object is arranged in the center of the circular path.

In an embodiment, it is provided that the guidance device has a rail system on which the radiation source and the radiation detector can be moved.

A rail system enables, in a particularly simple and precise manner, a movement of the radiation source and of the radiation detector along the movement path of the supporting device.

The invention also relates to an imaging device which contains a radiation source, a radiation detector and an inventive supporting device. An imaging device of this type is configured to utilize the aforementioned advantages of the inventive supporting device during an image recording in a surgical operating area.

Other features which are considered as characteristic for the invention are set forth in the appended claims.

Although the invention is illustrated and described herein as embodied in a supporting device and an intra-operative imaging device having the supporting device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE INVENTION

Figure 1:
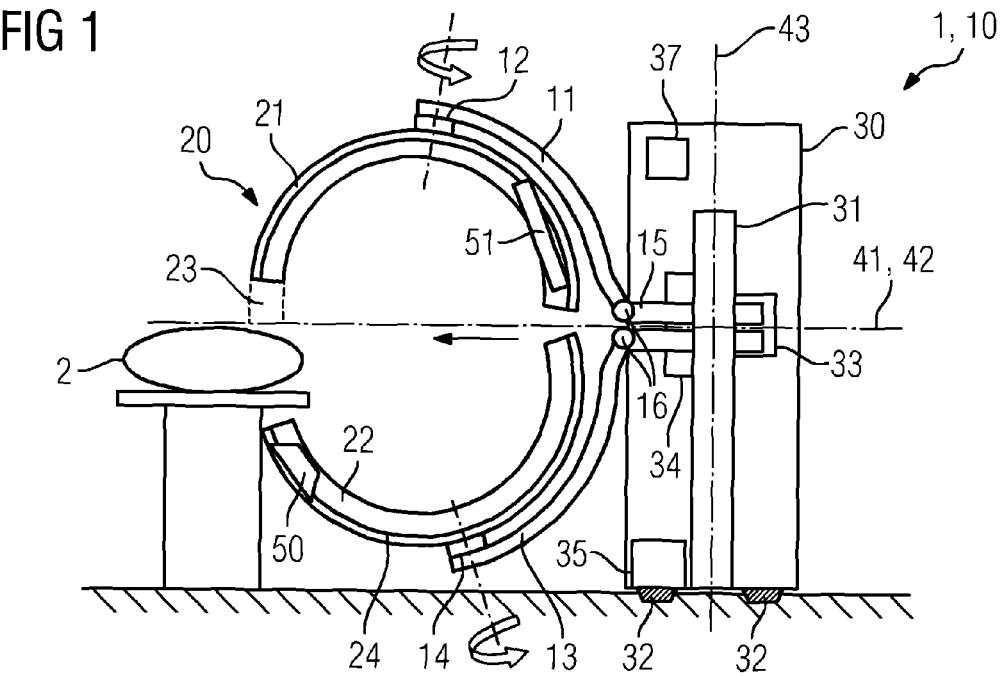
FIG. 1 is a diagrammatic, cross-sectional view through an imaging device having a supporting device in a second position according to the invention.

Referring now to the figures of the drawings in detail and first, particularly to FIG. 1 thereof, there is shown an imaging device 1 having an inventive supporting device 10 in a schematic representation. Also shown is an object under investigation 2.

The supporting device 10 has a base unit 30. The supporting device 10 also has a first support arm 11 and a second support arm 13. The support arms 11, 13 are arranged to be pivotable at the base unit 30 via joints 16.

The supporting device 10 also has a guidance device 20 which contains a first segment 21 and a second segment 22. It is also conceivable, however, for the guidance device 20 to be divided into more than two segments 21, 22.

The segment 21 is rotatably arranged at a rotary connection 12 at an end of the first support arm 11 remote from the joint 16. For example, an axle, a rotary bearing or another rotatable connection which can be loaded under tension, can be provided as the rotary connection 12. Furthermore, in one embodiment, the rotary connection 12 has a motorized drive for rotating the segment 21.

In a similar manner, the second segment 22 is rotatably arranged at a rotary connection 14 at an end of the second support arm 13 remote from the joint 16.

Figure 2:
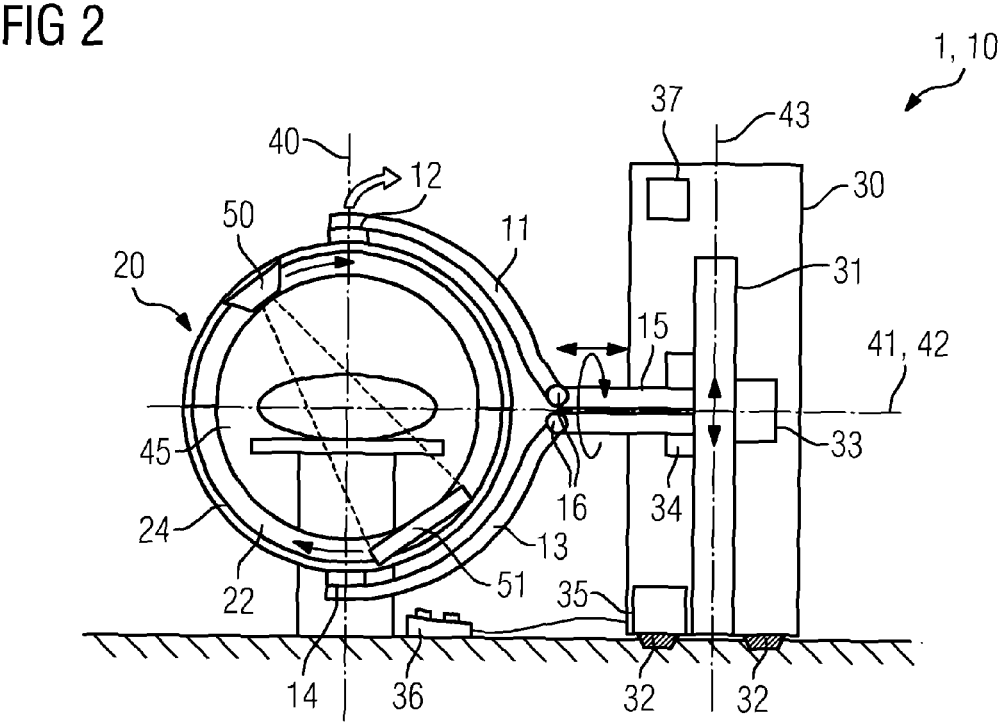
FIG. 2 is a diagrammatic, cross-sectional view through the imaging device having the supporting device in a first position.
Figure 3:
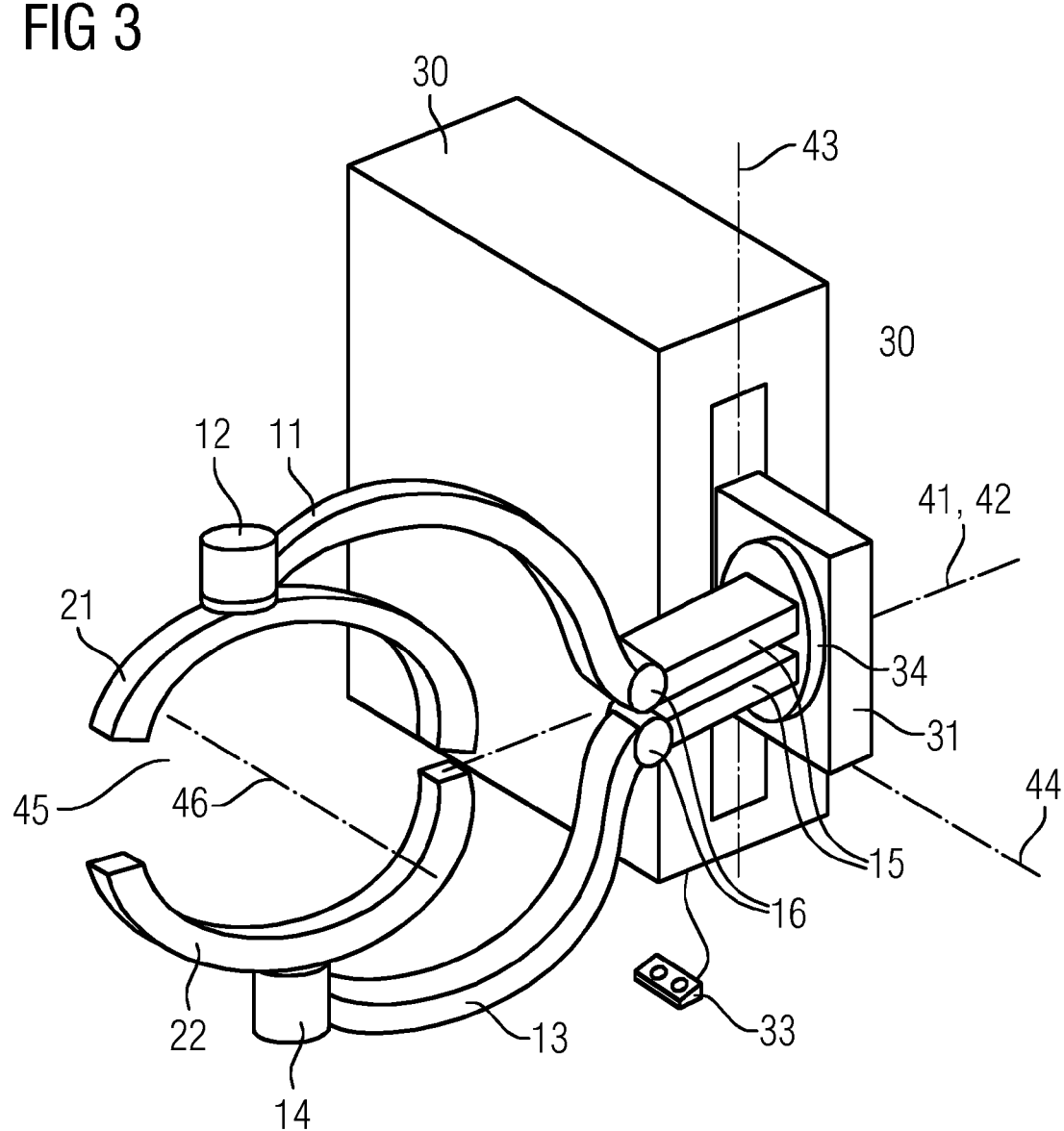
FIG. 3 is a diagrammatic, perspective view of the imaging device having the supporting device in the second position.

The support arms 11, 13 are pivotable relative to one another about the joints 16, so that the segments 21, 22 of the guidance device 20 are in contact with one another in a first position of the support arms 11, 13 so that the segments 21, 22 form a closed movement path enclosing an area 45. The first position is shown in FIG. 2. By a pivot movement about the joints 16, the first support arm 11 and the second support arm 13 can be moved into a second position such that the two segments 21, 22 are spaced apart from one another and an interruption 23 is produced in a closed movement path or curve, separating the two segments 21, 22 from one another. In this second position, shown in FIG. 1, it is possible to introduce an object under investigation 2 laterally through the interruption 23 from a region outside the movement path, into a region within the movement path.

Preferably, the pivot movement is carried out such that the two support arms 11 and 13 and the segments 21 and 22 arranged thereon are moved in one plane away from one another by a pivot movement about the joints 16. However, it is also conceivable that only one support arm and one segment, for example, the first support arm 11 and the first segment 21 are pivoted in one plane away from the second support arm 13 and the second segment 22. It is also possible that the movement of the two support arms 11, 13 and segments 21, 22 does not take place in one plane, but rather in two different planes which lie at an angle to one another.

In the second position, in which the first segment 21 is spaced apart from the second segment 22 and the interruption 23 is present, it is further conceivable that the first segment 21 is rotated about the rotary connection 12 in order to facilitate the introduction of the object under investigation 2 into the region 45 enclosed by the movement path.

In the first position, in which the first segment 21 and the second segment 22 are in contact with one another and form a closed movement path, the rotation axes of the first rotary connection 12 and the second rotary connection 14 are configured such that the two rotation axes lie coaxially over one another and both the segments 21, 22 are rotatable about a common first rotation axis 40.

The first rotation axis 40 extends through the area 45 enclosed by the movement path or at a slight distance therefrom on one side of the area 45, such that the projection of the rotation axis along a normal to the enclosed area 45 comes to lie on the area 45 itself. Preferably, the first rotation axis 40 is arranged centrally to the segments 21, 22 and extends through the area 45 itself. By this measure, it is possible to rotate the segments of the guidance device 20 through the largest possible angle about the first rotation axis 40 before the segments come into contact with an elongate object under investigation arranged within the movement path or an operating table.

The connection of the joints 16 to the base unit 30 is achieved by a telescopic extension 15, which is rotatably arranged at a linear axis 31 which, in turn, is arranged at the base unit 30.

By the telescopic extension 15, the support arms 11, 13 and the segments 21, 22 of the guidance device 20 can be moved along a first translation axis 42 in the direction toward the object under investigation 2. In a preferred embodiment, the first translation axis 42 is oriented horizontally. The guidance device 20 can thus be moved, in the second position with the movement path interrupted, from the side round the object under investigation.

The telescopic axis 15, in turn, is arranged to be rotatable about the first translation axis 42, so that the orientation of the area 45 about the first translation axis 42 can also be changed in relation to the object under investigation.

A linear axis 31 is also movable along a second translation axis 43 so that the guidance device 20 arranged thereon can also be moved along the second translation axis 43. In a preferred embodiment, the second translation axis 43 is oriented perpendicularly to the first translation axis 42 and perpendicularly to the floor, i.e. vertically, so that the guidance device 20 is also movable with respect to height.

The base unit 30 also has transport devices 32 which enable the base unit 30 to move along a third translation axis 44. Preferably, the third translation axis 44 is oriented perpendicularly to the first translation axis 42 and to the second translation axis 43 and is also oriented horizontally along a longitudinal direction of the object under investigation 2. Conceivable transport devices 32 are, for example, linear rails, telescopic extensions or wheels. For example, rails can be provided in the floor or, in the case of a hanging arrangement, on a ceiling of a room in which the supporting device 10 is put to use, the rails being in engagement with the wheels.

The three translation axes 42, 43 and 44 cover a three-dimensional space, so that the guidance device 20 can be moved to any point within the space.

In a preferred embodiment, a motor drive is provided for the rotary connections 12, 14, the telescopic extension 15 in translational and rotary motion, and the linear axis 31 and the transport device 32. The motor drive is preferably provided electrically, but can also be carried out pneumatically, hydraulically or by other measures. In this way, it is possible to control the movement of the guidance device 20 by operating elements 36, for example, foot pedals, so that the operation can be performed without jeopardizing the sterility in the surgical operating area. In one possible embodiment, the control of the drives can also be carried out by a control device 37, for example, by a computer. The computer can move the guidance device 20 in a targeted manner, by suitable control, into a particular position or back again into a previously assumed position. A control device 37 of this type also makes it possible to automate a movement, for example, for a scan in the longitudinal direction of the object under investigation 2, wherein the guidance device 20 is moved with the aid of the transport device 32 in the direction of the third translation axis 44 along the object under investigation. Finally, it is also conceivable that the control device 37 recognizes acoustic commands or gestures by an operator and carries out corresponding movements.

In one embodiment, the guidance device 20 has a rail system 24 which is arranged at the segments 21, 22. A radiation source 50 and a radiation detector 51 can be displaceably arranged at the rail system 24, so as to be movable along the movement path on a closed path round the object under investigation 2 when the support arms 11, 13 are in the first position and the segments 21, 22 form a closed movement path with the rail system provided thereon.

In the inventive imaging device 1, for example, a radiation source 50 and a radiation detector 51 are provided at the rail system 24 of the guidance device 20, positioned mutually opposed at the movement path, so that the radiation emitted by the radiation source 50 passes through the object under investigation 2 onto the radiation detector 51. In this way, individual radiographic images can be made at different angles, or sectional images can be made by combining a plurality of radiographic images recorded at different angles. For this purpose, the individual images are recorded while the radiation source 50 and the radiation detector 51 move synchronously on the movement path, which is preferably configured as a circular path. It is also possible to arrange a plurality of pairs of radiation sources 50 and radiation detectors 51 offset relative to one another by a peripheral angle and movable spaced apart from one another along the movement path in order to accelerate the image acquisition or to acquire images using different imaging methods simultaneously, for example at different X-ray photon energies.

In the preferred embodiment shown, the segments 21, 22 are configured to be circular arc-shaped, so that the radiation source 50 and the radiation detector 51 are arranged at a constant distance from one another and from an object under investigation 2 arranged at the center of the circular path.

The guidance device 20 can have a shell which surrounds the segments 21, 22. In the first, closed position, the first segment 21 and the second segment 22 form a hollow body, for example, a closed torus which surrounds the region within the movement path. In the first position, the moved parts, such as the radiation source 50 and the radiation detector 51 are arranged out of reach within the shell and are not accessible from outside. Using simple measures, for example, a sterile covering made from foils or other suitable materials, it is possible to prepare the guidance device 20 with the components contained therein according to the hygiene requirements in the surgical operating area.

A simultaneous movement of the radiation source 50 and the radiation detector 51 along the movement path of the guidance device 20 and along the third translation axis 44 is conceivable, wherein the area enclosed by the movement path is oriented essentially perpendicularly to the third translation axis 44. Thus, with the aid of the radiation source 50 and of the radiation detector 51, a spiral scan along an object under investigation 2 which lies, for example, on a surgical operating table can be acquired.

A simultaneous movement of the radiation source 50 and of the radiation detector 51 along the movement path of the guidance device 20 and along the second translation axis 43 is also conceivable, wherein the area enclosed by the movement path is oriented essentially perpendicularly to the second translation axis 43. Thus, with the aid of the radiation source 50 and the radiation sensor 51, a spiral scan can also be acquired along an object under investigation 2 or a patient who is, for example, standing or sitting on a chair.

In an embodiment, the guidance device 20 is detachably connected to the base unit 30. For this purpose, the telescopic extension 15 is arranged in a corresponding receptacle at the linear rail 31, in which the telescopic arm 15, once introduced, is locked. Locking is carried out with a locking element engaging in the telescopic arm 15, for example, a bolt. Other fastening possibilities are also conceivable, for example, bayonet fastenings which are locked by a rotation. It is also conceivable for the joints 16 to be configured to be releasable in that a connecting bolt about which a respective joint 16 is pivoted, is configured to be removable.

Although the invention has been illustrated and described in detail with the preferred exemplary embodiment, the invention is not restricted by the examples given and other variations may be derived by a person skilled in the art without departing from the protective scope of the invention.

The invention claimed is:

1. A supporting device for a radiation source and a radiation detector, the supporting device comprising:
   a base unit;
   a guidance device having at least one first segment and one second segment, said guidance device configured such that the radiation source and the radiation detector can be disposed at said guidance device and can be moved along a movement path, wherein an object under investigation can be disposed inside the movement path such that radiation emitted by the radiation source falls, through the object under investigation, onto the radiation detector;
   a first support arm;
   a first rotation connection disposed on said first support arm;

said first segment is rotatably disposed at said first rotation connection at said first support arm and said first support arm is rotatable at said base unit such that, by a pivot movement of said first support arm, said first segment can be moved from a first position in which the movement path is closed into a second position in which there is an interruption in the movement path and the object under investigation can be introduced from a region outside the movement path, through the interruption in the movement path, into a region inside the movement path.

2. The supporting device according to claim 1,
further comprising a second support arm at which said second segment of said guidance device is disposed;
further comprising a second rotary connection disposed on said second support arm;
wherein said second segment is rotatably disposed at said second rotary connection at said second support arm so that, in the first position in which the movement path is closed, said guidance device is rotatable about a connecting line of said first and second rotary connections; and
wherein the connecting line is a first rotation axis and has an intersection point with a normal to an area enclosed by the movement path.

3. The supporting device according to claim 2, wherein said first support arm and said second support arm are detachably connected to said base unit.

4. The supporting device according to claim 2, wherein said first support arm and said second support arm are rotatable relative to said base unit about a common second rotation axis which is oriented at an angle to the first rotation axis such that the orientation of the area enclosed by the movement path is rotatable in space.

5. The supporting device according to claim 2, wherein said first support arm and said second support arm have a device configured for changing a distance between said base unit and said guidance device in a direction of a first translation axis.

6. The supporting device according to claim 5, wherein said device for changing the distance are telescopic extensions.

7. The supporting device according to claim 5, further comprising a device for movement at which said first and the second support arms are disposed, wherein said device for movement is configured to move said first and second support arms relative to said base unit in a direction of a second translation axis, wherein the first translation axis and the second translation axis are disposed at an angle to one another.

8. The supporting device according to claim 7, wherein said device for movement along the second translation axis is a linear rail.

9. The supporting device according to claim 7, further comprising transport device disposed at said base unit, said transport devices configured to move the supporting device along a third translation axis, wherein the third translation axis is disposed at an angle to the first translation axis and the second translation axis.

10. The supporting device according to claim 9, further comprising a motorized drive configured to move the supporting device along at least one of the first translation axis, the second translation axis or the third translation axis.

11. The supporting device according to claim 10, wherein said motorized drive has a control device configured to move the supporting device into a pre-definable position along at least one of the first translation axis, the second translation axis or the third translation axis.

12. The supporting device according to claim 1, wherein said first and second segments of said guidance device have an arc form.

13. The supporting device according to claim 1, wherein the closed movement path is circular in shape.

14. The supporting device according to claim 1, wherein said guidance device has a rail system at which the radiation source and the radiation detector can be moved.

15. An imaging device, comprising:
a radiation source;
a radiation detector; and
a supporting device containing:
   a base unit;
   a guidance device having at least one first segment and one second segment, said guidance device configured such that said radiation source and said radiation detector can be disposed at said guidance device and can be moved along a movement path, wherein an object under investigation can be disposed within the movement path such that radiation emitted by said radiation source falls, through the object under investigation, onto said radiation detector;
   a first support arm;
   a first rotation connection disposed on said first support arm;
   said first segment is rotatably disposed at said first rotation connection at said first support arm and said first support arm is rotatable at said base unit such that, by a pivot movement of said first support arm, said first segment can be moved from a first position in which the movement path is closed into a second position in which there is an interruption in the movement path and the object under investigation can be introduced from a region outside the movement path, through the interruption in the movement path, into a region inside the movement path.

* * * * *